(12) United States Patent
Bare et al.

(10) Patent No.: US 9,364,630 B2
(45) Date of Patent: *Jun. 14, 2016

(54) TRACHEOSTOMY VALVES AND RELATED METHODS

(71) Applicant: Passy-Muir, Inc., Irvine, CA (US)

(72) Inventors: Rex O. Bare, Lake Forest, CA (US); Andrew J. Scherer, Trabuco Canyon, CA (US)

(73) Assignee: Passy-Muir, Inc., Irvine, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/458,852

(22) Filed: Aug. 13, 2014

(65) Prior Publication Data

US 2015/0182715 A1    Jul. 2, 2015

Related U.S. Application Data

(63) Continuation of application No. 13/244,067, filed on Sep. 23, 2011, now abandoned, which is a continuation of application No. 11/830,573, filed on Jul. 30, 2007, now Pat. No. 8,051,856.

(51) Int. Cl.
*A61M 16/04* (2006.01)
*A61M 16/20* (2006.01)

(52) U.S. Cl.
CPC ......... *A61M 16/0468* (2013.01); *A61M 16/208* (2013.01); *A61M 2206/11* (2013.01); *Y10T 137/789* (2015.04)

(58) Field of Classification Search
CPC ............... A61M 16/0465; A61M 16/0468; Y10T 137/7888; Y10T 137/789; Y10T 137/7891; Y10T 137/7859; Y10T 137/7862; F16K 15/14; F16K 15/148; F16K 15/144
USPC ............................................. 137/854, 516.11
See application file for complete search history.

(56) References Cited

U.S. PATENT DOCUMENTS 3,009,266 A    11/1961  Brook
3,137,299 A     6/1964  Tabor
(Continued)

FOREIGN PATENT DOCUMENTS

JP    S61-130678    6/1986
JP    62-502103     8/1987
(Continued)

OTHER PUBLICATIONS

Advisory Action issued in U.S. Appl. No. 13/244,067, dated Feb. 24, 2014.
(Continued)

*Primary Examiner* — Steven Douglas
*Assistant Examiner* — LaToya M Louis
(74) *Attorney, Agent, or Firm* — Knobbe Martens Olson & Bear LLP

(57) ABSTRACT

The embodiments of the present tracheostomy valves include a flexible diaphragm abutting a rib shaped substantially as a flat plate. Opposite the rib, the diaphragm abuts a boss and forms an uninterrupted seal therewith. As the tracheostomized patient inhales, the diaphragm bends about the rib, interrupting the seal and allowing air to flow smoothly into the valve. The features of the various embodiments contribute to a positive seal at all times except during inhalation, and low resistance to airflow through the valve during inhalation.

15 Claims, 12 Drawing Sheets

(56) References Cited

U.S. PATENT DOCUMENTS

| | | | |
|---|---|---|---|
| 3,376,659 A | 4/1968 | Asin | |
| 3,410,003 A | 11/1968 | Sovijarvi | |
| 3,693,624 A | 9/1972 | Shiley et al. | |
| 3,802,096 A | 4/1974 | Matern | |
| 3,827,440 A * | 8/1974 | Birch et al. | 128/207.16 |
| 3,844,290 A * | 10/1974 | Birch et al. | 128/207.16 |
| 4,029,105 A * | 6/1977 | Faust | 128/207.17 |
| 4,040,428 A | 8/1977 | Clifford | |
| 4,200,097 A * | 4/1980 | Hobbs et al. | 604/213 |
| 4,209,919 A | 7/1980 | Kirikae et al. | |
| 4,325,366 A | 4/1982 | Tabor | |
| 4,416,273 A | 11/1983 | Grimes | |
| 4,484,896 A | 11/1984 | Kohnke | |
| 4,494,252 A | 1/1985 | Chaoui | |
| 4,506,665 A * | 3/1985 | Andrews et al. | 128/202.27 |
| 4,510,933 A | 4/1985 | Wendt et al. | |
| 4,538,607 A * | 9/1985 | Saul | 128/207.16 |
| 4,582,058 A | 4/1986 | Depel et al. | |
| 4,649,913 A * | 3/1987 | Watson | 128/207.14 |
| 4,683,916 A | 8/1987 | Raines | |
| 4,759,356 A | 7/1988 | Muir | |
| 4,773,865 A | 9/1988 | Baldwin | |
| 5,005,568 A * | 4/1991 | Loescher et al. | 128/202.28 |
| 5,055,052 A | 10/1991 | Johnsen | |
| 5,195,896 A | 3/1993 | Sweeney et al. | |
| 5,238,409 A | 8/1993 | Brault et al. | |
| 5,312,259 A | 5/1994 | Flynn | |
| 5,314,339 A | 5/1994 | Aponte | |
| 5,582,166 A * | 12/1996 | Lee | 128/207.14 |
| 5,727,594 A * | 3/1998 | Choksi | 137/859 |
| 5,738,095 A | 4/1998 | Persson | |
| 5,806,515 A | 9/1998 | Bare et al. | |
| 6,193,751 B1 | 2/2001 | Singer | |
| 6,334,441 B1 | 1/2002 | Zowtiak et al. | |
| 6,921,417 B2 | 7/2005 | Persson | |
| 7,025,784 B1 | 4/2006 | Blom et al. | |
| 7,240,676 B2 | 7/2007 | Rutter | |
| 7,252,110 B2 | 8/2007 | Semeia | |
| 7,311,119 B2 | 12/2007 | Takehana et al. | |
| 8,051,856 B2 | 11/2011 | Bare et al. | |
| 2004/0182446 A1 | 9/2004 | Semeia | |
| 2006/0118190 A1 | 6/2006 | Takehana et al. | |

FOREIGN PATENT DOCUMENTS

| | | |
|---|---|---|
| JP | S63-96848 | 6/1988 |
| JP | 2000-511458 | 9/2000 |
| JP | 2003-501141 | 1/2003 |
| JP | 2006-509601 | 3/2006 |
| WO | WO 86/05102 | 2/1986 |
| WO | WO 98/43692 | 10/1998 |
| WO | WO 00/16840 | 3/2000 |
| WO | WO 02/074377 | 9/2002 |
| WO | WO 03/061531 | 7/2003 |

OTHER PUBLICATIONS

Decision of Rejection issued in Japanese Application No. 2010-520163, dated Dec. 17, 2013.
Decision of Rejection issued in Japanese Application No. 2013-078613, dated Dec. 17, 2013.
Extended European Search Report issued in European Application No. 08826674.7, dated Jun. 6, 2013.
Final Office Action issued in U.S. Appl. No. 11/830,573, dated Apr. 27, 2011.
Final Office Action issued in U.S. Appl. No. 13/244,067, dated Dec. 19, 2012.
Final Office Action issued in U.S. Appl. No. 13/244,067, dated Nov. 19, 2013.
International Search Report for International Application No. PCT-US2008-071654 mailed on Nov. 12, 2008.
Notice of Allowance issued in Japanese Application No. 2010-520163, dated Jun. 16, 2014.
Notice of Allowance issued in Japanese Application No. 2013-078613, dated Jun. 16, 2014.
Notice of Allowance issued in U.S. Appl. No. 11/830,573, dated Sep. 8, 2011.
Notice of Abandonment issued in U.S. Appl. No. 13/244,067, dated Jan. 2, 2015.
Notice of Panel Decision from Pre-Appeal Brief Review issued in U.S. Appl. No. 13/244,067, dated May 21, 2014.
Office Action issued in U.S. Appl. No. 11/830,573, dated Oct. 5, 2010.
Office Action issued in Japanese Application No. 2010-520163, dated Jan. 4, 2013.
Office Action issued in U.S. Appl. No. 13/244,067, dated Aug. 20, 2012.
Office Action issued in U.S. Appl. No. 13/244,067, dated May 21, 2013.
Office Action issued in Japanese Application No. 2010-520163, dated Jul. 30, 2013.
Office Action issued in Japanese Application No. 2013-078613, dated Jul. 30, 2013.
Office Action issued in Japanese Application No. 2014-085717, dated Feb. 9, 2015.
Office Action issued in Canadian Application No. 2,694,942, dated Aug. 15, 2014.
Supplementary European Search Report for European Application No. 86901722, dated May 3, 1988, in 10 pages.
Supplementary European Search Report issued in European Application No. 08826674.7, dated Jun. 25, 2013.

\* cited by examiner

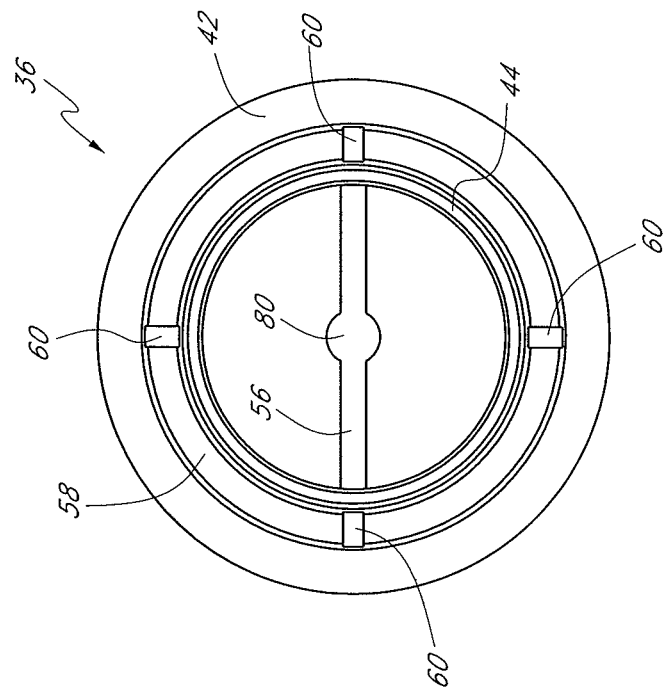
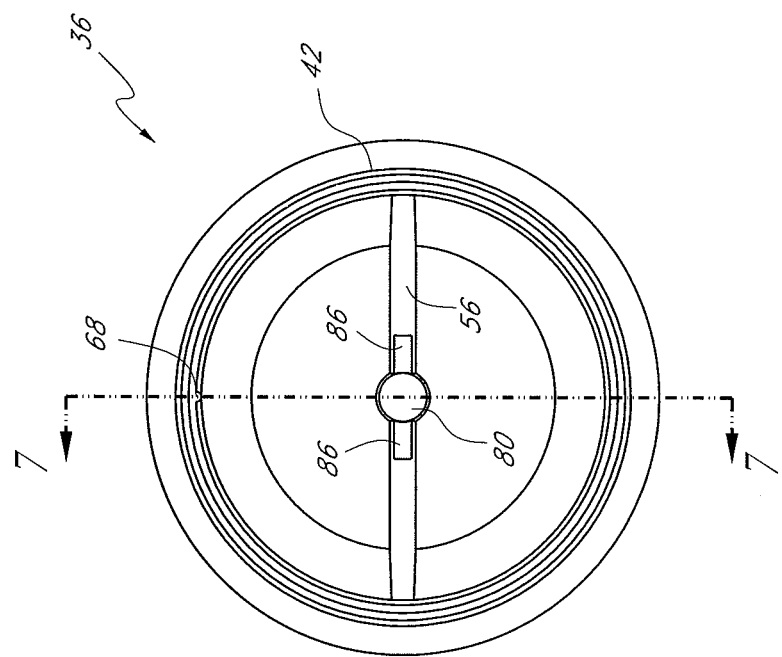
FIG. 9
FIG. 8

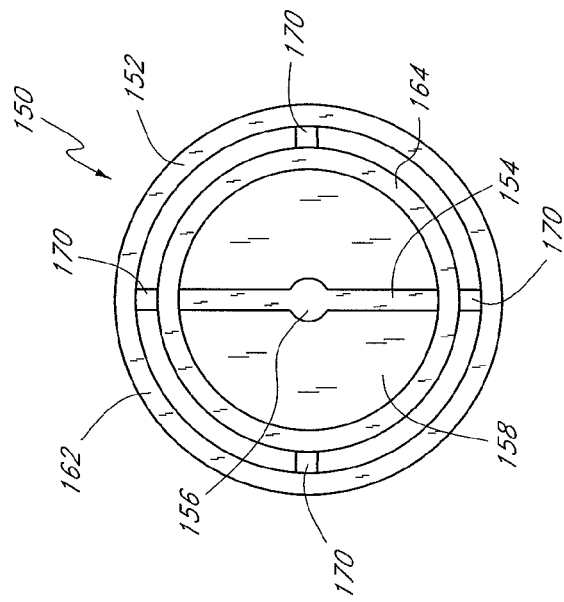
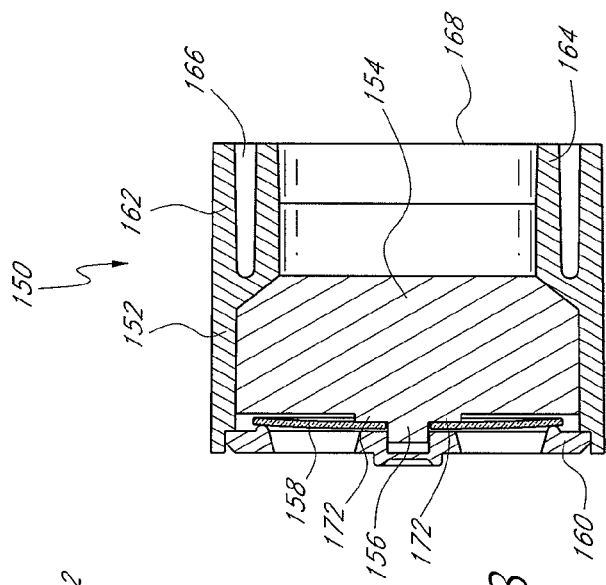
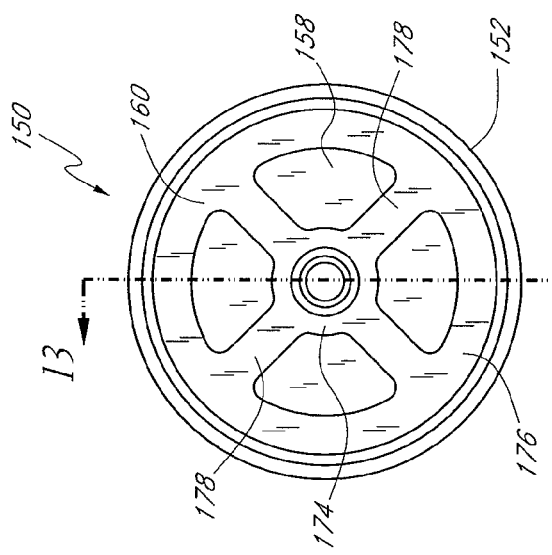
FIG. 15
FIG. 13
FIG. 14

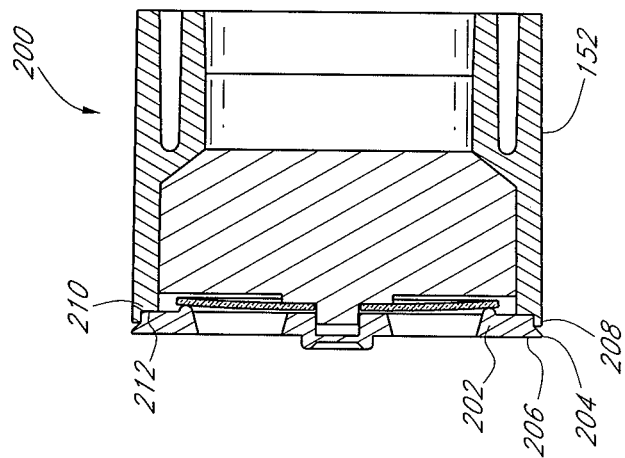
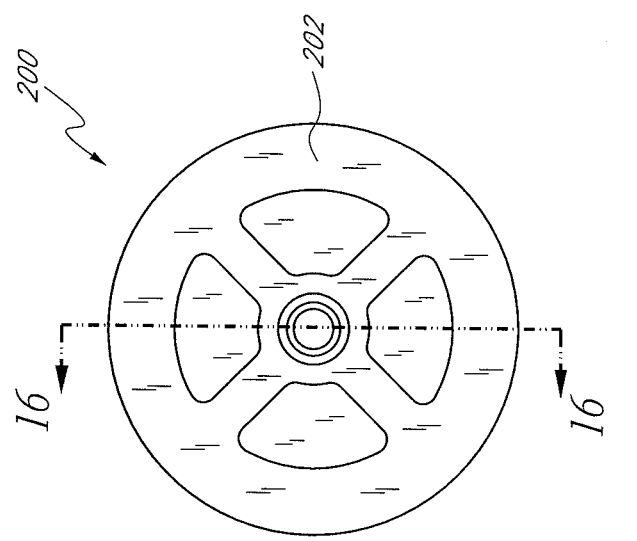

TRACHEOSTOMY VALVES AND RELATED METHODS

CROSS REFERENCE TO RELATED APPLICATIONS

This application is a continuation of U.S. patent application Ser. No. 13/244,067, filed on Sep. 23, 2011, which is a continuation of U.S. patent application Ser. No. 11/830,573, filed on Jul. 30, 2007 and issued as U.S. Pat. No. 8,051,856 on Nov. 8, 2011, each of which is hereby incorporated by reference in its entirety.

BACKGROUND OF THE INVENTION

1. Field of the Invention

The present invention relates to valves and methods for use with tracheostomized patients.

2. Description of the Related Art

U.S. Pat. No. 4,759,356, the entirety of which is incorporated by reference herein, describes a tracheostomy valve unit. The valve unit is securable to one end of a tracheostomy tube assembly to regulate air flow through the tube. The valve unit remains closed when the tracheostomized patient exhales, and at all other times except when the patient inhales. When the patient inhales, the valve opens to allow air to flow through the tracheostomy tube to the patient's lungs.

An outer end of the valve includes a support to which a flexible diaphragm is secured. The diaphragm selectively seals the valve in response to the inhalation and exhalation of the patient. A rivet passes through the center of the diaphragm and the center of the support to secure these two components to one another. The rivet also seats the diaphragm against a seating ring on the support to preload the diaphragm and create an effective closure that maintains a positive, uninterrupted contact all along the seating ring at all times except when the patient inhales.

When properly manufactured, the tracheostomy valve unit described in the '356 patent is an effective apparatus for blocking outward air flow through the patient's tracheostomy tube, and for allowing inward air flow through the tube. However, the rivet must be precisely placed in order to preload the diaphragm and create the effective closure described above. If the rivet does not pull the diaphragm far enough toward the seating ring the diaphragm will not be properly preloaded and the valve will not be sealed at rest. On the other hand, if the rivet pulls the diaphragm too far toward the seating ring the diaphragm will be overloaded and will require too much pressure to open. In extreme cases the diaphragm may even wrinkle, which causes gaps to develop between the diaphragm and the seating ring. The gaps, of course, compromise the sealing ability of the diaphragm.

As described in the '356 patent, the process of placing the rivet involves a heat-staking step. "The effective length of rivet 20 is established during installation by blocking head 20a of the rivet with an adjustable support while at the same time heat-staking end 20c. Adjustment of the adjustable support then compresses rivet 20 and forms heat-staked end 20c, which mounts the diaphragm to support 16 and preloads diaphragm 18." (col. 9, ll. 52-58) Unfortunately, the heat-staking is rather imprecise, as the position of the heat-staked end 20c is affected by the temperature of the heat-staking apparatus and the length of time that heat is applied to the heat-staked end 20c. These variables are difficult to control with the precision necessary to properly place the rivet every time. There is also a tendency for melted plastic to stick to the tip of the heat-staking apparatus, which further complicates control over the process. Thus, a high percentage of the tracheostomy valve units are rejected during the manufacturing process, which in turn raises the cost of manufacturing the valve units.

SUMMARY OF THE INVENTION

The preferred embodiments of the present tracheostomy valves and related methods have several features, no single one of which is solely responsible for their desirable attributes. Without limiting the scope of these valves and methods as expressed by the claims that follow, their more prominent features will now be discussed briefly. After considering this discussion, and particularly after reading the section entitled "Detailed Description of the Preferred Embodiments," one will understand how the features of the preferred embodiments provide advantages, which include ease of manufacture, reliable and repeatable deformation of the diaphragm, smooth airflow through the valve unit during inhalation, and an uninterrupted seal preventing airflow through the valve unit at all times except during inhalation.

One embodiment of the present tracheostomy valves and related methods comprises a tracheostomy valve unit configured to cooperate with a tracheostomy tube insertable within a patient's trachea. The valve unit comprises a valve body having a first end, a second end and a fluid passageway extending therethrough. The first end is configured to be operably connected with the tracheostomy tube. A flexible diaphragm is positioned within the fluid passageway spaced from the first end of the valve body. The diaphragm has a first face and a second face opposite the first face. A rib is positioned within the fluid passageway. At least a portion of the rib abuts the first face of the diaphragm. A spacing between the diaphragm and the valve body first end is greater than a spacing between the rib and the valve body first end. At least a portion of the rib defines an imaginary plane that intersects at least a portion of the diaphragm in an imaginary line.

Another embodiment of the present tracheostomy valves and related methods comprises a tracheostomy valve unit configured to cooperate with a tracheostomy tube insertable within a patient's trachea. The valve unit comprises a valve body having a first end, a second end and a fluid passageway extending therethrough. The first end is configured to be operably connected with the tracheostomy tube. A rib shaped as a substantially flat plate is positioned within the fluid passageway and extends between opposite inner surfaces of the valve body along a diameter thereof. A flexible diaphragm is positioned within the fluid passageway spaced from the first end of the valve body. The diaphragm has a first face and a second face opposite the first face. At least a portion of an edge of the rib abuts the first face of the diaphragm. A spacing between the diaphragm and the valve body first end is greater than a spacing between the rib and the valve body first end.

Another embodiment of the present tracheostomy valves and related methods comprises a method of alleviating physiological dysfunction and improving bodily function in a patient who has been subjected to tracheostomization, where the dysfunction results from the tracheostomization and the function is impaired by the tracheostomization, the patient having a neck-opening into the patient's trachea, the neck opening being adapted to admit air into the trachea. The method comprises the steps of: (1) inserting into the trachea via the neck opening a tracheostomy tube, the tracheostomy tube having a tracheal end adapted to be received in the trachea, a proximal end adapted to be external to the patient's body, and a fluid passageway extending therethrough, the fluid passageway having a tube inlet at the proximal end and a tube outlet at the tracheal end in the patient's trachea; (2) inserting into the trachea the tracheostomy tube such that the tracheal end is received in the patient's trachea and the proximal end is external to the patient's body, the tube thus being configured to conduct air to the patient's trachea from the inlet to the outlet via the fluid passageway; (3) operatively securing to the proximal end of the tracheostomy tube a tracheostomy valve unit, the tracheostomy valve unit having a first end configured for operative connection to the proximal end of the tracheostomy tube, a second end, a valve unit inlet located at the second end of the valve unit, conducting means for permitting airflow therethrough from the valve unit inlet through the valve unit and then through the tube to the patient's trachea when the patient inhales, and blocking means making positive, uninterrupted closure contact with the valve unit inlet and thereby entirely blocking airflow through the conducting means from the tube and through the valve inlet at all times when the patient exhales and at all other times except when the patient inhales; and (4) fluidically connecting the valve first end to the proximal end of the tracheostomy tube and thereby permitting airflow from the valve unit inlet through the valve unit and then through the tube inlet to the patient's trachea when the patient inhales and entirely blocking airflow through the conducting means from the tube inlet and through the valve unit inlet to the ambient air at all times when the patient exhales and at all other times except when the patient inhales. As the patient inhales a pressure difference across the blocking means bends the blocking means around an imaginary line extending across the blocking means, thereby breaking the positive, uninterrupted closure contact with the valve unit inlet and permitting air to flow from the ambient through the valve unit inlet and into the valve unit.

Another embodiment of the present tracheostomy valves and related methods comprises a tracheostomy valve unit configured to cooperate with a tracheostomy tube insertable within a patient's trachea. The valve unit comprises a valve body having a proximal end, a distal end and a fluid passageway extending therethrough. The proximal end is configured to be operably connected with the tracheostomy tube. A rib is positioned within the fluid passageway adjacent the distal end, the rib being contiguous with the valve body. A flexible diaphragm is positioned within the fluid passageway distally from the rib. The diaphragm has a proximal face and a distal face. A cap is operably secured to the valve body distally from the diaphragm. The cap including a seating ring. At least a portion of the rib abuts the proximal face of the diaphragm and the seating ring abuts the distal face of the diaphragm. The rib and seating ring deform the diaphragm to create an uninterrupted positive seal at a junction between the diaphragm and the seating ring.

BRIEF DESCRIPTION OF THE DRAWINGS

The preferred embodiments of the present tracheostomy valves and related methods, illustrating its features, will now be discussed in detail. These embodiments depict the novel and non-obvious tracheostomy valves shown in the accompanying drawings, which are for illustrative purposes only. These drawings include the following figures, in which like numerals indicate like parts:

FIG. 8 is a front elevational view of the valve body of FIG. 7;

FIG. 9 is a rear elevational view of the valve body of FIG. 7;

FIG. 13 is a cross-sectional view of another embodiment of the present tracheostomy valves taken along the line 13-13 of FIG. 14;

FIG. 14 is a front elevational view of the tracheostomy valve of FIG. 13;

FIG. 15 is a rear elevational view of the tracheostomy valve of FIG. 13;

FIG. 16 is a cross-sectional view of another embodiment of the present tracheostomy valves taken along the line 16-16 of FIG. 17;

FIG. 17 is a front elevational view of the tracheostomy valve of FIG. 16;

DETAILED DESCRIPTION OF THE PREFERRED EMBODIMENTS

Figure 1:
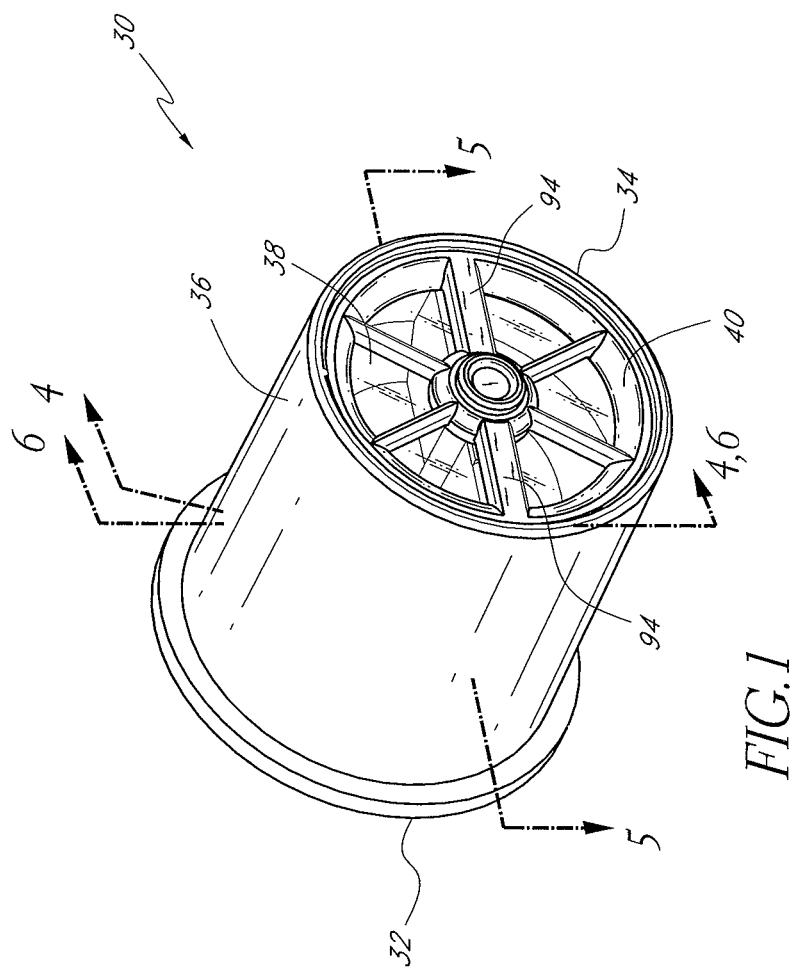
FIG. 1 is a front perspective view of one embodiment of the present tracheostomy valves.

FIGS. 1-6 illustrate one embodiment of the present tracheostomy valve. The valve 30 is shaped substantially as a tapered elongate cylinder, and includes a proximal end 32 and a distal end 34 (FIG. 1). As used herein, the terms proximal and distal refer to proximity to a tracheostomized patient. Thus, for example, the proximal end 32 of the valve 30 is so named because it is relatively closer to the patient when the valve 30 is properly engaged with a tracheostomy tube that is positioned within a stoma in a patient.

Figure 2:
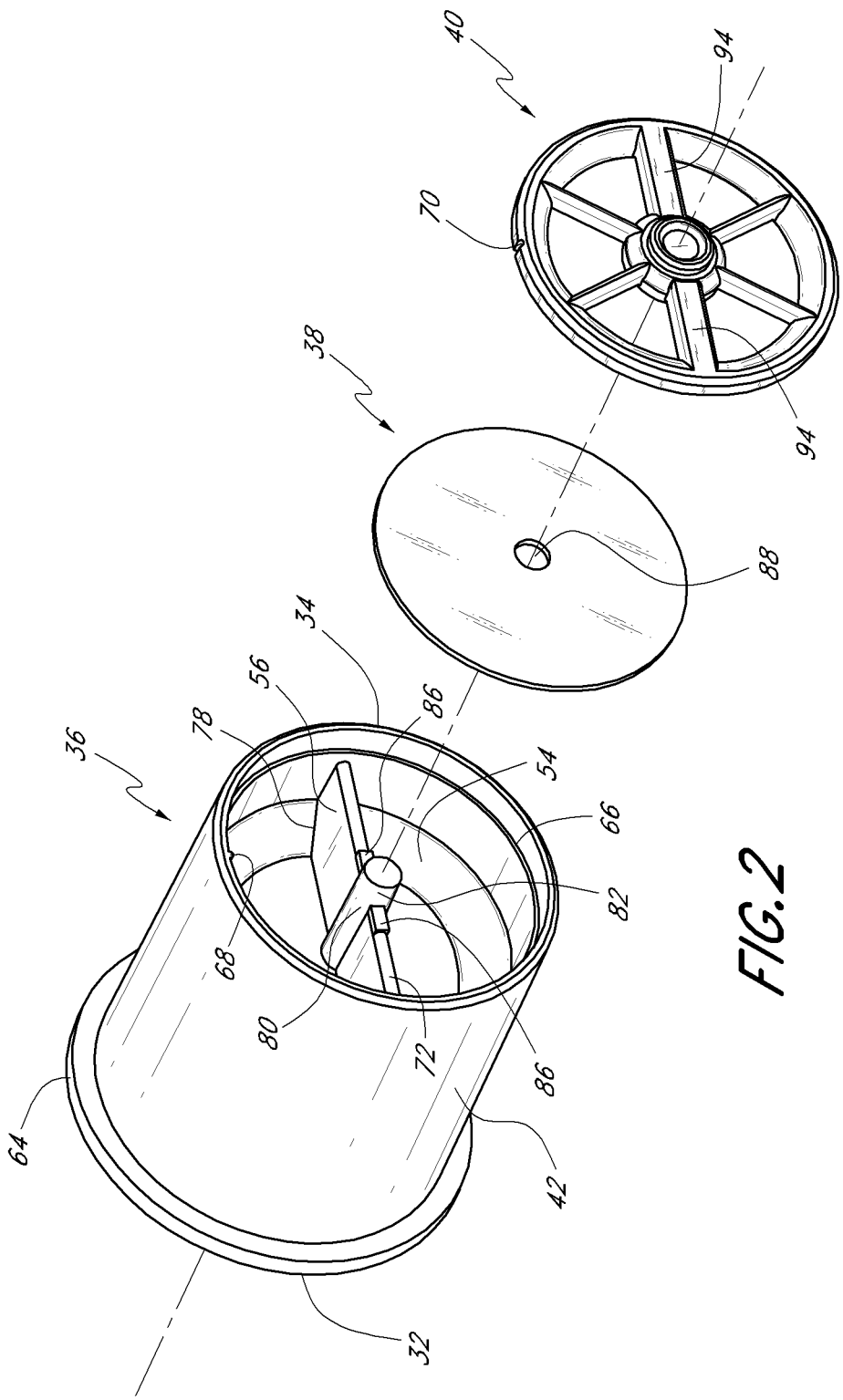
FIG. 2 is an exploded front perspective view of the tracheostomy valve of FIG. 1.
Figure 3:
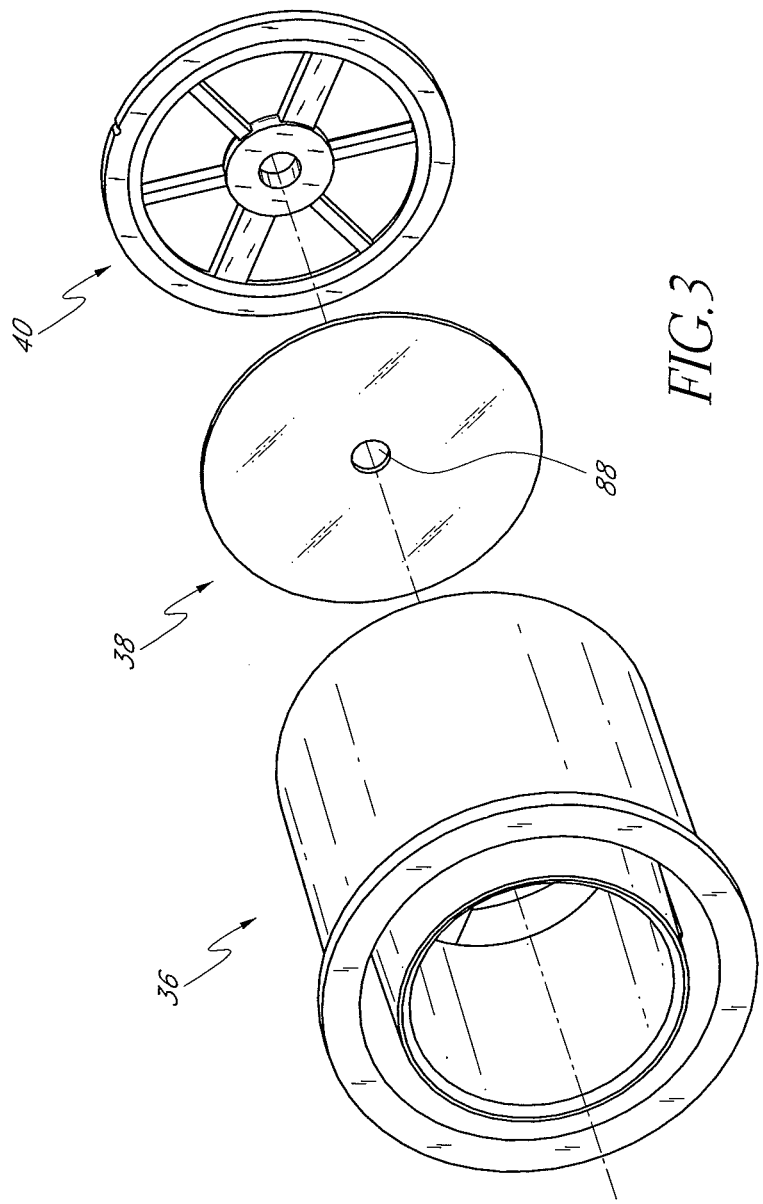
FIG. 3 is an exploded rear perspective view of the tracheostomy valve of FIG. 1.
Figure 7:
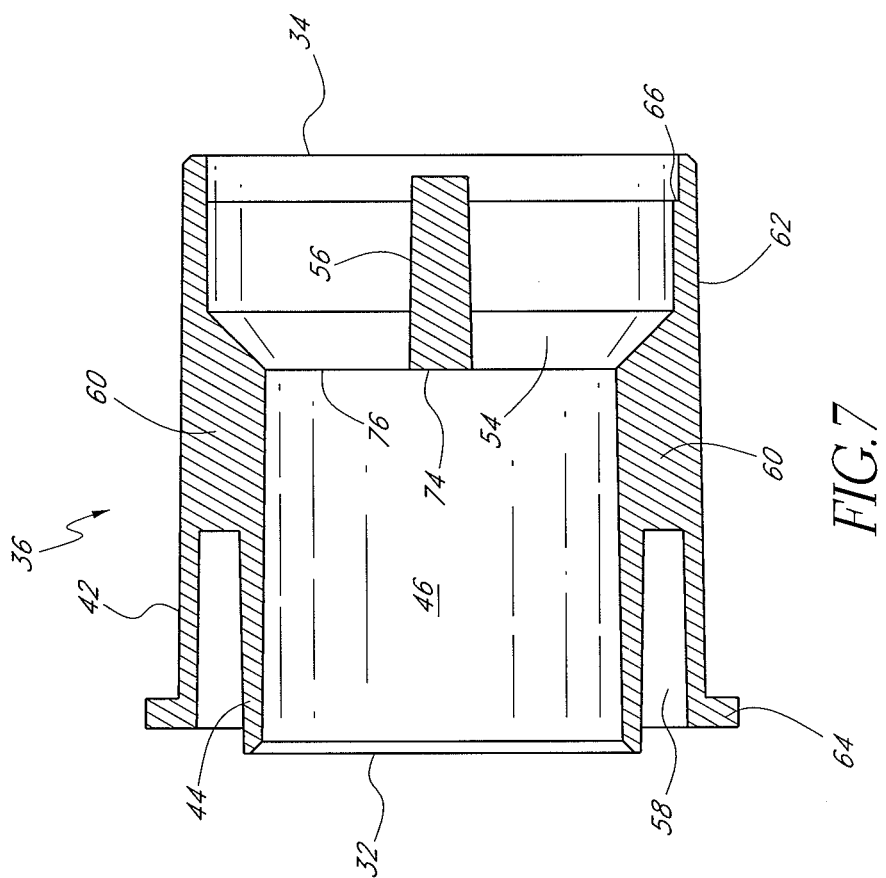
FIG. 7 is a cross-sectional view of a valve body of the tracheostomy valve of FIG. 1 taken along the line 7-7 of FIG. 8.

With reference to FIGS. 2 and 3, the valve 30 comprises a valve body 36, a diaphragm 38 and a cap 40. FIGS. 7-9 illustrate the valve body 36 in detail. In the illustrated embodiment, the valve body 36 comprises, substantially, a tapered cylindrical outer body 42 and a tapered cylindrical inner body 44. An interior portion of the inner body 44 defines a fluid passageway 46 (FIG. 7) that conducts air through the valve 30, as described in detail below.

Figure 4:
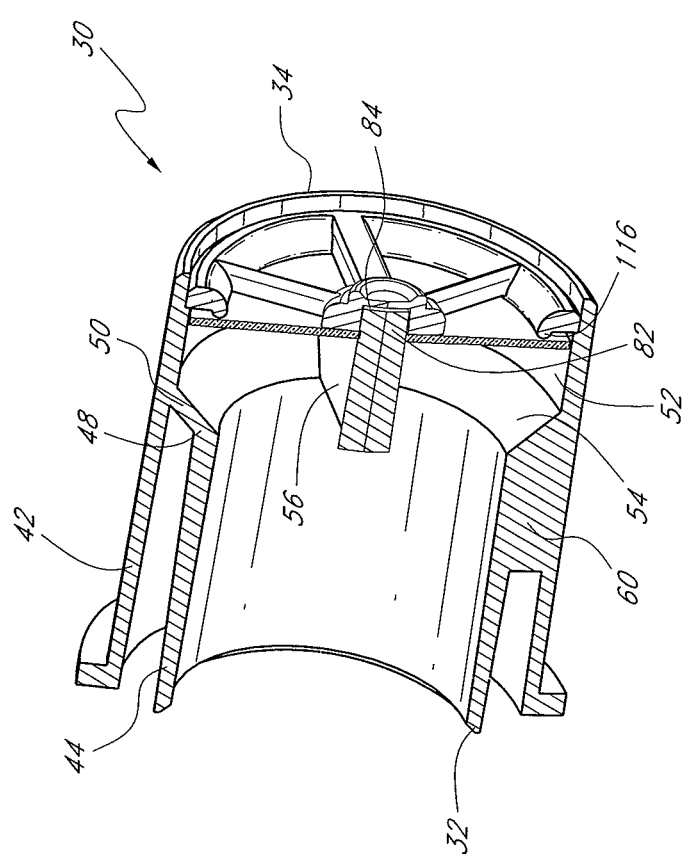
FIG. 4 is a front perspective, cross-sectional view of the tracheostomy valve of FIG. 1.

With reference to FIG. 4, the inner body 44 resides within the outer body 42, and a distal end 48 of the inner body 44 includes an outwardly extending flange 50 that merges with an inner surface 52 of the outer body 42 at a location spaced from the distal end 34 of the outer body 42. In the illustrated embodiment, the inner body flange 50 extends at an angle of approximately 45° outward from the inner body 44 and toward the distal end 34 of the valve 30. Those of ordinary skill in the art will appreciate that the inner body flange 50 could extend at any angle from the inner body 44. However, shallower angles create lesser resistance to airflow past the flange, while steeper angles create greater resistance. Thus, relatively shallow angles are preferred, and 45° provides acceptable airflow. A surface of the flange 50 that faces distally forms a shoulder 54 that supports a rib 56, as explained in detail below.

With reference to FIG. 7, an outer diameter of the inner body 44 is less than an inner diameter of the outer body 42, such that a cylindrical cavity 58 exists between the inner body 44 and the outer body 42. A plurality of regularly spaced splines 60 (FIGS. 7 and 9) extends across the cavity 58 and joins the inner body 44 to the outer body 42. In the illustrated embodiment, four splines 60 are shown and each spline 60 extends from the distal end 48 of the inner body 44 to a location spaced from the proximal end 32 of the valve 30 (FIG. 4). However, those of ordinary skill in the art will appreciate that fewer or more splines 60 may be provided, and that the splines 60 may extend a shorter or a longer distance along the cavity 58. The splines 60 advantageously increase the rigidity of the valve body 36 and help to maintain the round shape of the valve body 36. However, those of ordinary skill in the art will appreciate that no splines need be provided.

With reference to FIG. 7, the wall thickness of the inner body 44 increases in the proximal-to-distal direction. Thus, in that same direction the inner diameter of the inner body 44 gradually decreases and the outer diameter of the inner body 44 gradually increases. The inner body 44 is thus configured to mate with a tracheostomy tube (not shown) in a sliding friction fit. In one embodiment the tracheostomy tube is received within the inner body 44, while in another embodiment the inner body 44 is received within the tracheostomy tube. In yet another embodiment an adapter (not shown) is disposed between the valve 30 and the tracheostomy tube so that the inner body 44 and the tracheostomy tube do not directly engage one another. The inner body 44 may be sized to mate with commonly used tracheostomy tubes of known diameters and wall thicknesses. For example, in one embodiment the inner body 44 includes a 15 mm ISO taper. However, the inner body 44 may be produced in a variety of sizes to fit any tracheostomy application. Furthermore, those of ordinary skill in the art will appreciate that in some embodiments the inner body 44 may not include tapered surfaces.

With reference to FIG. 7, in the illustrated embodiment an outer surface 62 of the outer body 42 tapers inwardly from the proximal end 32 to the distal end 34. The tapering facilitates the placement of the valve 30 in line with a ventilator. For example, the proximal end 32 of the valve body 36 may receive a tracheostomy tube, as described above, and the distal end 34 of the valve body 36 may receive a tube associated with the ventilator, with the tube overlapping the distal end 34 in a sliding friction fit. The outer body 42 may be sized to mate with commonly used tubes of known diameters and wall thicknesses. For example, in one embodiment the outer body 42 includes a 22 mm ISO taper. However, the outer body 42 may be produced in a variety of sizes and tapers to fit any application. Furthermore, those of ordinary skill in the art will appreciate that in some embodiments the outer body 42 may not include a tapered outer surface 62.

With reference to FIGS. 2 and 7, a proximal end 32 of the outer body 42 includes an outwardly extending flange 64. The flange 64 advantageously increases the rigidity of the valve body 36 and helps to maintain the round shape of the valve body 36. However, those of ordinary skill in the art will appreciate that the flange 64 need not be provided.

With continued reference to FIGS. 2 and 7, the outer body 42 includes an inwardly extending annular ledge 66. The ledge 66 extends around the inside circumference of the outer body 42 and is spaced a short distance from the distal end 34. The ledge 66 provides a seat for the cap 40, as explained in detail below. With reference to FIGS. 2 and 8, a key 68 extends inwardly from an inner surface of the outer body 42 at the distal end 34 thereof. The key 68 mates with a key slot 70 (FIGS. 2 and 10) on the cap 40, as explained in detail below.

With reference to FIGS. 2 and 7, a rib 56 extends across the valve body 36. The rib 56 is shaped substantially as a flat plate, and extends between inner surfaces of the outer body 42, across the diameter thereof. A distal edge 72 (FIG. 2) of the rib 56 is spaced in the proximal direction from the ledge 66. A proximal edge 74 (FIG. 7) of the rib 56 lies in an imaginary plane defined by a proximal edge 76 of the shoulder 54, such that proximal corners 78 of the rib 56 extend along the shoulder 54 (FIG. 2). Those of ordinary skill in the art will appreciate that the rib 56 could be shaped and/or configured differently. For example, the rib 56 could extend a shorter distance or a longer distance along a length of the valve body 36, and/or the rib 56 need not abut the shoulder 54.

With reference to FIGS. 2, 8 and 9, in the illustrated embodiment a substantially cylindrical post 80 intersects the rib 56. A longitudinal axis of the post 80 substantially coincides with a longitudinal axis of the valve body 36. A diameter of the post 80 is greater than a thickness of the rib 56. A height of the post 80 is greater than a length of the rib 56, such that a distal extension portion 82 (FIG. 2) of the post 80 extends distally from the distal edge 72 of the rib 56. The distal extension portion 82 mates with a recess 84 (FIG. 12) in the cap 40, as explained in detail below. Those of ordinary skill in the art will appreciate that the post 80 could be shaped and/or configured differently. For example, the post 80 may be taller or shorter, and/or have a smaller or larger diameter, and/or have a different cross-sectional shape.

To either side of the post 80, the distal edge 72 of the rib 56 includes first and second biasing protrusions 86. The protrusions 86 bear against center portions of the diaphragm 38 to bias the diaphragm 38 against the cap 40, as described in detail below. The biasing contributes to a complete, uninterrupted seal around the entirety of the cap 40, as explained in detail below.

Figure 5:
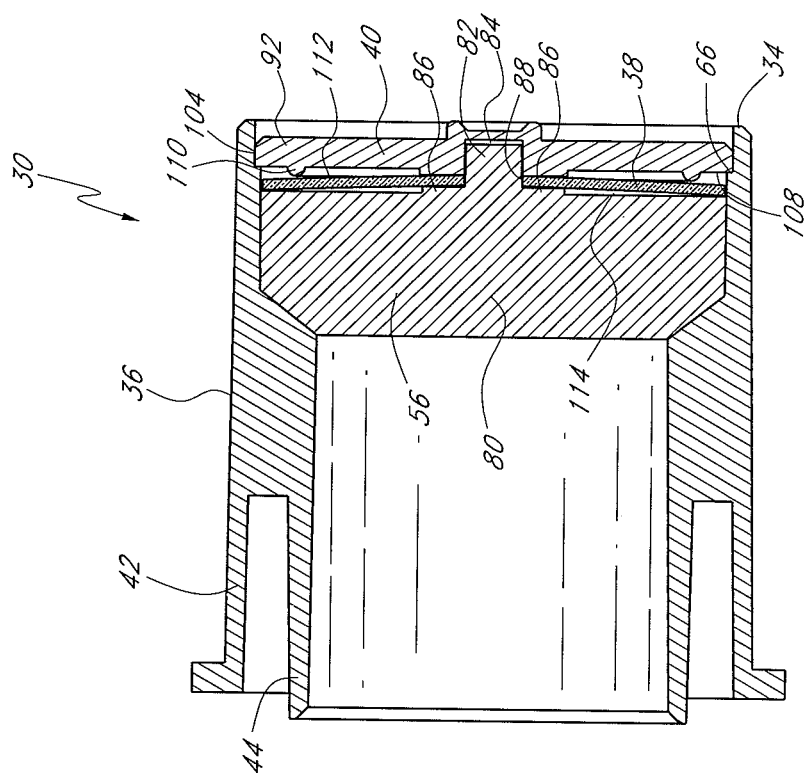
FIG. 5 is a cross-sectional view of the tracheostomy valve of FIG. 1, taken along the line 5-5 in FIG. 1.

For clarity, and with reference to FIG. 5, the valve body 36, including the inner body 44 and the outer body 42, are illustrated as a first unitary piece, and the rib 56 and the post 80 are illustrated as a second unitary piece. Those of ordinary skill in the art will appreciate that the valve body 36 and the rib 56/post 80 may be formed as separate pieces that are, for example, adhered or welded to one another, or secured by any other suitable means. Those of ordinary skill in the art will also appreciate that the valve body 36, the rib 56 and the post 80 may be formed as a single, unitary piece.

In one embodiment, the valve body 36 may be constructed of a plastic or another similar material. In one such embodiment the valve body 36 is constructed of Acrylonitrile Butadiene Styrene (ABS plastic). Those of ordinary skill in the art will appreciate that the valve body 36 could be constructed of alternative materials, such as acrylics, polymers (such as polypropylene and polyethylene) and metals. The valve body 36 may be made by any of a variety of processes, such as molding, injection molding, casting and machining.

With reference to FIGS. 2 and 3, the diaphragm 38 comprises a relatively thin disk with a central aperture 88. The aperture 88 is configured and positioned to receive the distal extension portion 82 of the post 80, such that the diaphragm 38 seats upon the protrusions 86. Portions of the diaphragm 38 may contact the distal edge 72 of the rib 56.

In the illustrated embodiment, the diaphragm 38 is circular. However, those of ordinary skill in the art will appreciate that the diaphragm 38 could have any shape that is configured to cooperate with the valve body 36 and the cap 40 to create a seal at or near the distal end 34 of the valve 30. The diaphragm 38 is preferably flexible so that it can deform as the patient inhales, thereby breaking the seal and allowing air to flow through the valve 30. The diaphragm 38 is also preferably capable of forming a seal when in contact with the cap 40. In one embodiment, the diaphragm 38 is constructed of silicone. However, those of ordinary skill in the art will appreciate that other materials could be used instead.

Figure 11:
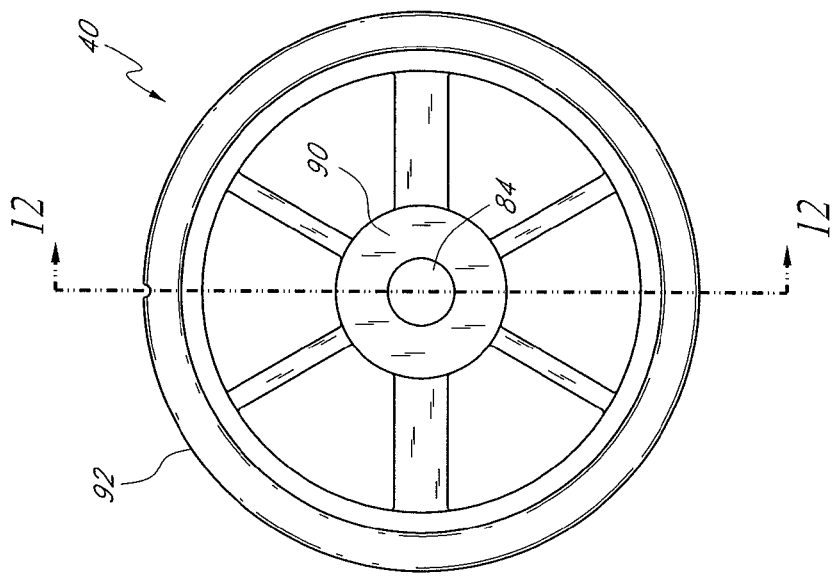
FIG. 11 is a rear elevational view of the cap of FIG. 10.
Figure 12:
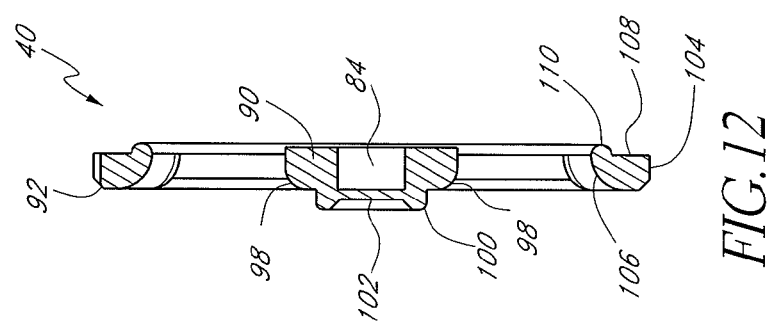
FIG. 12 is a cross-sectional view of the cap of FIG. 10 taken along the line 12-12 of FIG. 11.
Figure 10:
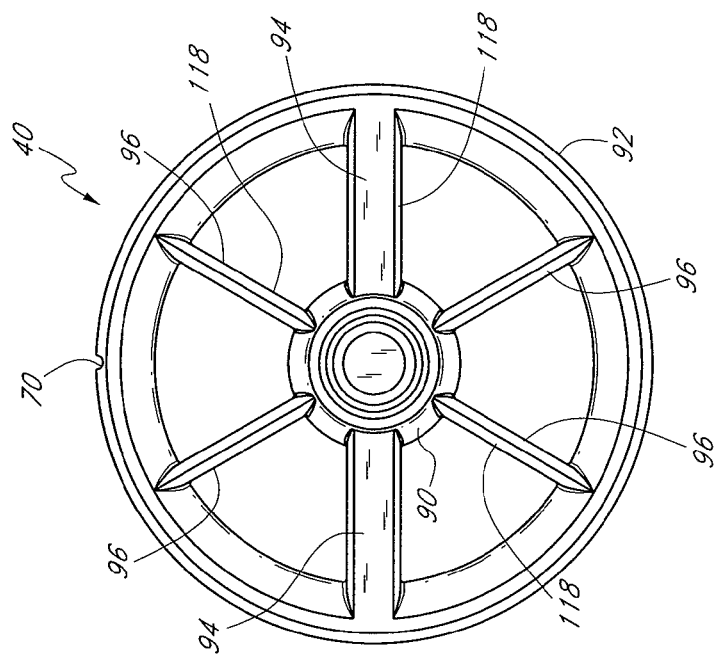
FIG. 10 is a front elevational view of a cap of the tracheostomy valve of FIG. 1.

FIGS. 10-12 illustrate in detail the cap 40. The cap 40 resembles a wheel, and includes a central hub 90, an outer rim 92, and a plurality of spokes 94, 96 extending between the hub 90 and the rim 92. In the illustrated embodiment, six spokes 94, 96 are provided, and neighboring spokes 94, 96 are separated by approximately 60°. However, those of ordinary skill in the art will appreciate that fewer or more spokes could be provided, and that the spokes need not be regularly spaced. Furthermore, in the illustrated embodiment two of the spokes 94 are relatively thick, and four of the spokes 96 are relatively thin. However, those of ordinary skill in the art will appreciate that more of the spokes may be relatively thick, or more of the spokes may be relatively thin. In at least some of the spokes 94, 96, it is advantageous for a cross-section of the spoke to taper outwardly in the distal-to-proximal direction. This configuration reduces resistance to airflow through the cap 40, as described in detail below.

In the illustrated embodiment, the hub 90 is circular and includes a cylindrical recess 84 in a proximal surface thereof (FIG. 12). The recess 84 receives the distal extension portion 82 of the post 80 on the valve body 36 in a mating engagement, as described in detail below. The cross-sectional shape and/or depth of the recess 84 may be varied to enable the recess 84 to mate with the post 80. A distal, outer edge 98 of the hub 90 includes a taper that reduces resistance to airflow through the cap 40, as described in detail below. A distal face of the hub 90 includes a boss 100 having a central depression 102.

In the illustrated embodiment, the rim 92 is circular and includes an irregular cross-section (FIG. 12) having a flat outer surface 104 (facing away from the hub 90) and a tapered inner surface 106 (facing toward the hub 90). However, those of ordinary skill in the art will appreciate that the rim 92 could have virtually any shape, such as oval, elliptical or square. Those of ordinary skill in the art will also appreciate that the rim 92 could have virtually any cross-sectional shape. However, the tapered inner surface 106, in which the inner diameter of the rim 92 decreases in the distal-to-proximal direction, advantageously reduces resistance to airflow through the cap 40, as described in detail below.

In the illustrated embodiment, the outer surface of the rim 92 includes a key slot 70 (FIG. 10) that mates with the key 68 on the valve body 36, as shown in FIGS. 1 and 2. The mating key 68 and key slot 70 ensure that the cap 40 is properly aligned with the valve body 36. When properly aligned, the wider spokes 94 on the cap 40 align with the rib 56. This configuration reduces the resistance to airflow through the valve 30, as described in detail below. Those of ordinary skill in the art will appreciate that neither the key 68 nor the key slot 70 need be provided. Those of ordinary skill in the art will also appreciate that more keys and mating key slots could be provided on the valve body 36 and the cap 40, respectively. Those of ordinary skill in the art will also appreciate that the locations of the key(s) and key slot(s) could be reversed. That is, the cap 40 could be provided with one or more keys, and the valve body 36 could be provided with one or more mating key slots.

In the illustrated embodiment, a proximal surface 108 of the rim 92 includes an annular boss 110 (FIG. 12). The boss 110 is located adjacent the inner surface 106 of the rim 92, and extends entirely around the rim 92. In the assembled valve 30, the boss 110 bears against outer portions of the diaphragm 38, as described in detail below. The boss 110 thus deforms and pre-loads the diaphragm 38 to create an uninterrupted seal around the entire boss 110, as described in detail below.

The cap 40 may be constructed of the same material as the valve body 36, or of a different material. For example, the cap 40 may be constructed of any of the materials described above with respect to the valve body 36. However, those of ordinary skill in the art will appreciate that the cap 40 could be constructed of other materials.

With reference to FIGS. 1-6, in the assembled valve 30 the distal end 34 of the valve body 36 receives the diaphragm 38 with the distal extension portion 82 (FIG. 5) of the post 80 extending through the aperture 88. With particular reference to FIG. 5, the cap 40 nests within the distal end 34, sandwiching the diaphragm 38 between the rib 56 and the cap 40. An outer edge of the proximal surface 108 of the rim 92 abuts the ledge 66 on the valve body 36. The ledge 66 thus helps to positively locate the cap 40 within the valve body 36. Reliable and repeatable location of the cap 40 helps to ensure that the diaphragm 38 is properly biased against the boss 110 on the cap 40, and advantageously contributes to a low rejection rate during the manufacturing process. The outer surface 104 of the rim 92 may engage the inner surface of the valve body 36 in a friction fit to help maintain the cap 40 within the valve body 36. Alternatively, or in addition, adhesive may be applied during the manufacturing process in any region where the cap 40 abuts the valve body 36. The adhesive may be UV curable, for example. Alternatively, or in addition, the abutting surfaces of the cap 40 and the valve body 36 may be welded.

As shown in FIGS. 4 and 5, the distal extension portion 82 of the post 80 extends into the recess 84 in the proximal face of the hub 90. The distal extension portion 82 may engage the recess 84 in a friction fit to help maintain the cap 40 within the valve body 36. Alternatively, or in addition, adhesive may be applied to the distal extension portion 82 and/or within the recess 84 during the manufacturing process. Alternatively, or in addition, the distal extension portion 82 may be welded within the recess 84.

FIG. 5 illustrates a cross-sectional view of the valve 30. The section plane of FIG. 5 passes through the rib 56 and coincides with an imaginary plane defined by the rib 56, as shown by the line 5-5 in FIG. 1. The diaphragm 38 occupies a space between the rib 56 and the cap 40. In the illustrated embodiment, a thickness of the diaphragm 38 is greater than a perpendicular distance between a first imaginary plane that abuts the boss 110 and a second imaginary plane that abuts the biasing protrusions 86. The boss 110 thus bears against outer portions of the distal face 112 of the diaphragm 38 while the biasing protrusions 86 bear against central portions of the proximal face 114 of the diaphragm 38. The forces applied to the diaphragm 38 by the boss 110 and the biasing protrusions 86 balance one another and bend the diaphragm 38 out of plane. The diaphragm 38 is in a state of equilibrium in which the proximal face 114 is slightly concave and the distal face 112 is slightly convex. Furthermore, the continuous force applied to the diaphragm 38 by the boss 110 helps to maintain a positive and uninterrupted seal at the junction of the boss 110 and the diaphragm 38. This seal prevents air from leaking outward through the valve 30, which provides several advantages, including improved speech, olfaction, oxygenation and swallowing, decreased nasal and oral secretions and lessening of chronic infections.

In one embodiment, the bias applied to the diaphragm 38 is equivalent to approximately 8 to 15 mm of water head. This amount of bias effectively seats the diaphragm 38 against the boss 110 to maintain positive, uninterrupted contact at the junction therewith. In one embodiment, a bias of 8 to 15 mm of water head can be obtained with a diaphragm 38 constructed of silicone having a hardness of 40 Shore A, the diaphragm having a diameter of approximately 0.75" and a thickness of approximately 0.015", where the center of the diaphragm 38 is displaced approximately 0.002" to 0.003" out of plane relative to the edge of the diaphragm 38.

The configuration of the present valve 30 advantageously overcomes the shortcomings of the tracheostomy valve unit described in U.S. Pat. No. 4,759,356. As outlined above, the manufacturing process for the valve described in the '356 patent involves a heat-staking step. This step is affected by the temperature of the heat-staking apparatus and the length of time that heat is applied to the heat-staked end. These variables are difficult to control with the precision necessary to properly place the rivet every time. In the present valve 30, there is no heat-staking step. Thus, proper loading of the diaphragm 38 depends only upon the dimensional tolerances of the valve components. These tolerances are easier to control than the variables involved in heat-staking. Thus, the present valve 30 achieves a lower rejection rate during manufacturing, which in turn lowers the costs of manufacturing the valve 30.

Figure 6:
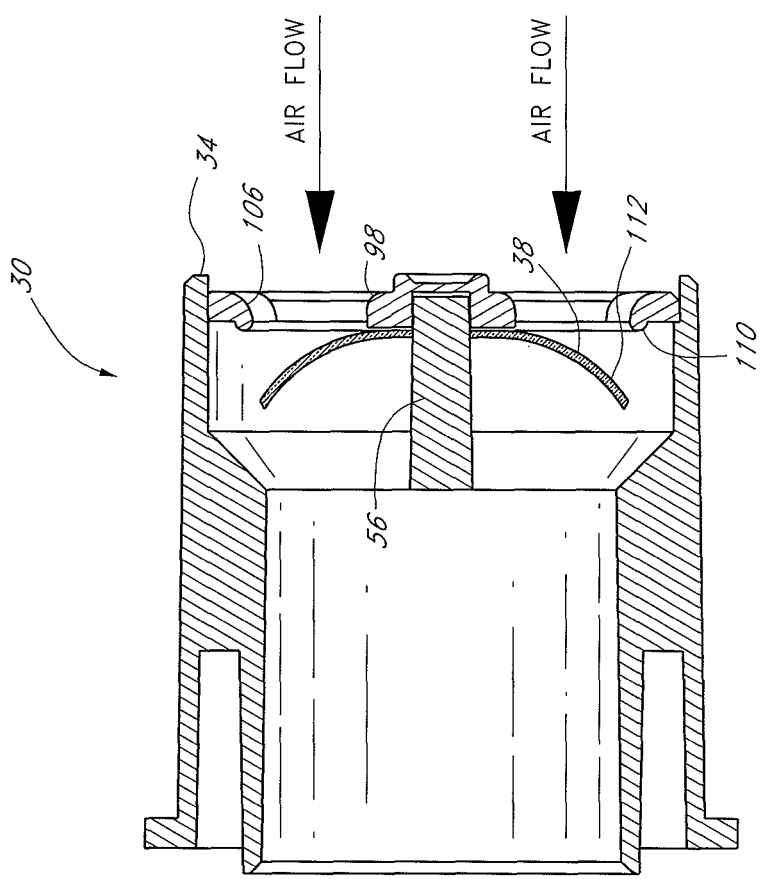
FIG. 6 is a cross-sectional view of the tracheostomy valve of FIG. 1, taken along the line 6-6 in FIG. 1, and illustrating a diaphragm of the valve in a flexed state as it appears when the patient inhales.

FIG. 6 illustrates a cross-sectional view of the valve 30. The section plane of FIG. 6 passes through the rib 56 and is perpendicular to an imaginary plane defined by the rib 56, as shown by the line 6-6 in FIG. 1. In FIG. 6, the diaphragm 38 is deformed as it appears when the patient inhales. As the patient inhales he or she creates a net pressure difference across the diaphragm 38, with a greater pressure bearing against the distal face 112. The force of the air bearing against the distal face 112 deforms the diaphragm 38 and breaks the seal at the junction of the boss 110 and the diaphragm 38. Air thus flows around the diaphragm 38 and into the valve 30 through the distal end 34, as illustrated by the arrows in FIG. 6.

Because the rib 56 is substantially planar, an imaginary plane defined by the rib 56 intersects the diaphragm 38 in an imaginary line, and the diaphragm 38 bends about this line as the patient inhales. The diaphragm 38 thus deforms in a predictable and repeatable way. At the moment just prior to inhalation, the air pressure on the distal face 112 is uniform over the entire exposed area of the distal face 112. Thus, as inhalation begins the air bearing against the distal face 112 creates a bending moment for the diaphragm 38 about the rib 56. The magnitude of the bending moment is greatest at the two locations on diaphragm 38 that abut the boss 110 and are spaced farthest from the rib 56, since the pressure on the distal face is uniform, and the longest moment arms occur at these two points 116 (FIG. 4). In the illustrated embodiment, since the rib 56 is substantially planar and the boss 110 is circular, the two points 116 on the boss 110 spaced farthest from the rib 56 coincide with an imaginary line drawn perpendicular to the rib 56 and passing through the post 80. Thus, as the patient inhales the seal between the diaphragm 38 and the boss 110 always breaks first at these two points 116, and the diaphragm 38 bends in a smooth arc around the rib 56, as illustrated in FIG. 6. This predictable and repeatable breaking and bending provides low resistance to the valve opening. The low resistance in turn contributes to low resistance to airflow through the valve and reduces or eliminates any sounds made by the diaphragm 38. When the patient stops inhaling, the diaphragm 38 returns to its original configuration of FIG. 5, thereby resealing the valve 30 at the junction with the boss 110.

As described above, an imaginary plane defined by the rib 56 intersects the diaphragm 38 in an imaginary line, and the diaphragm 38 bends about this line as the patient inhales. (FIG. 6) Therefore, air flowing into the valve 30 through the distal end 34 passes to either side of the rib 56. Any obstructions, such as spokes 94, 96, on either side of the rib 56 will increase resistance to airflow. By contrast, spokes 94, 96 that align with the rib 56 provide little, if any, additional impedance to airflow beyond that which is already created by the rib 56 itself. Therefore, the greatest resistance to airflow through the valve 30 is provided when none of spokes 94, 96 are aligned with the rib 56, and the resistance can be reduced if the narrower spokes 96 align with the rib 56, and the least resistance can be achieved if the two wider spokes 94 align with the rib 56. As described above, the key 68 on the valve body 36 and the key slot 70 on the cap 40 ensure that the wider 94 spokes align with the rib 56.

The least resistance to airflow through the valve 30 is achieved when the airflow is laminar. Turbulence will cause the diaphragm 38 to flutter, which will disrupt the airflow. The shapes of some portions of the cap 40 facilitate laminar airflow. For example, the inner surface 106 of the rim 92 (facing toward the hub 90) tapers inward so that the inner diameter of the rim 92 decreases in the distal-to-proximal direction (FIGS. 6 and 12). Also, side edges 118 of the spokes taper outward in the distal-to-proximal direction (FIGS. 10 and 11), and the hub 90 includes a rounded distal outer edge 98 (FIGS. 6 and 12). Each of these features reduces resistance to airflow, thereby facilitating smooth, laminar airflow through the cap 40.

FIGS. 13-15 illustrate another embodiment of the present tracheostomy valves. The valve 150 of FIGS. 13-15 is substantially similar to the valve 30 illustrated in FIGS. 1-12, and includes a valve body 152, a rib 154, a post 156, a diaphragm 158 and a cap 160. For clarity, the diaphragm 158 has been illustrated as if it were opaque. However, those of ordinary skill in the art will appreciate that the diaphragm 158 could be transparent. The valve body 152 includes an outer valve body 162 and an inner valve body 164, with a tapered cylindrical cavity 166 formed between these two members at a proximal end 168 of the valve body 152. A plurality of regularly spaced splines 170 extends across the cavity 166 and joins the inner body 164 to the outer body 162. The rib 154 is shaped and configured similarly to the rib 56 described above, and includes first and second biasing protrusions 172.

With reference to FIGS. 13 and 14, the cap 160 is shaped and configured similarly to the cap 40 described above, and includes a hub 174, a rim 176 and a plurality of spokes 178 extending between the hub 174 and the rim 176. In the cap 160 of FIGS. 14-16, however, only four spokes 178 are provided, and neighboring spokes are spaced by approximately 90°. Those of ordinary skill in the art will appreciate that fewer or more spokes 178 could be provided, and that the spokes 178 need not be regularly spaced. Furthermore, in the illustrated embodiment each of the spokes 178 is of a uniform thickness. However, those of ordinary skill in the art will appreciate that some of the spokes may have thicknesses that differ from the thickness of one or more other spokes. In the embodiment of FIGS. 14-16, the cap 160 is illustrated with no key slot, and the valve body 152 is illustrated with no key. However, those of ordinary skill in the art will appreciate that a key slot and a key may be provided on these components.

FIGS. 16 and 17 illustrate another embodiment of the present tracheostomy valves. The valve 200 of FIGS. 16 and 17 is substantially similar to the valve 150 illustrated in FIGS. 13-15. However, in the valve 200 of FIGS. 16 and 17 the cap 202 includes an outwardly extending flange 204 at a distal end 206 thereof that extends outward adjacent a distal face 208 of the valve body 152. The cap 202 nests within the distal end 210 of the valve body 152, and seats upon a ledge 212 that extends around the valve body 152. However, the ledge 212 is spaced a lesser distance from the distal face 208 of the valve body 152, as compared to the valve 150 illustrated in FIGS. 13-15.

Figure 20:
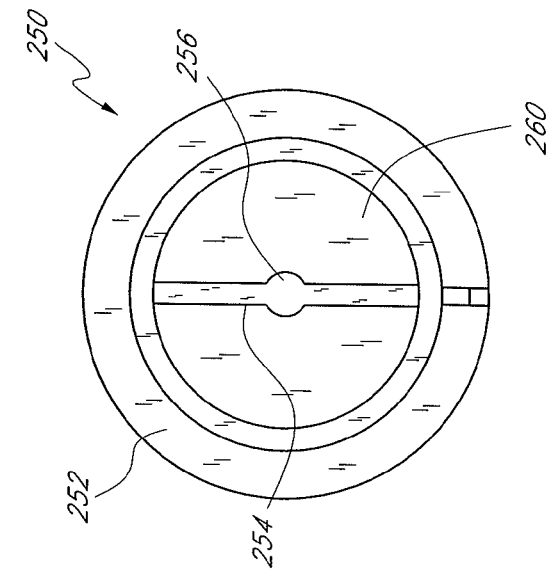
FIG. 20 is a rear elevational view of the tracheostomy valve of FIG. 18.
Figure 18:
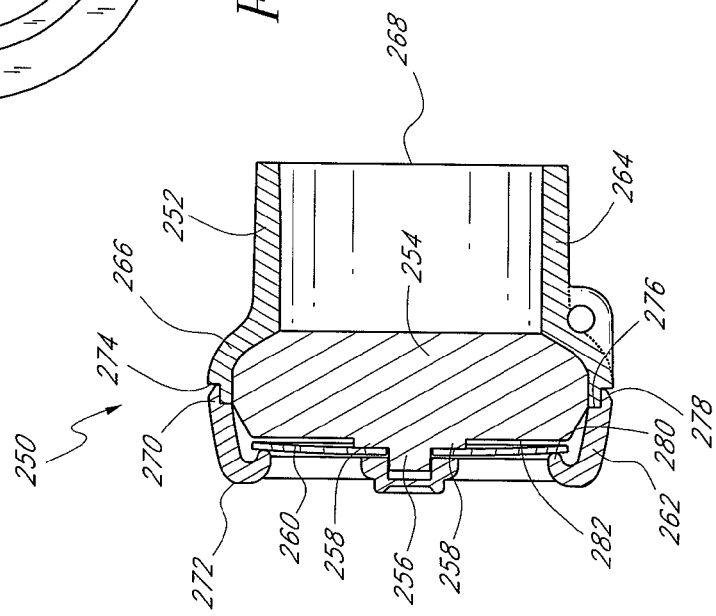
FIG. 18 is a cross-sectional view of another embodiment of the present tracheostomy valves taken along the line 18-18 of FIG. 19.
Figure 19:
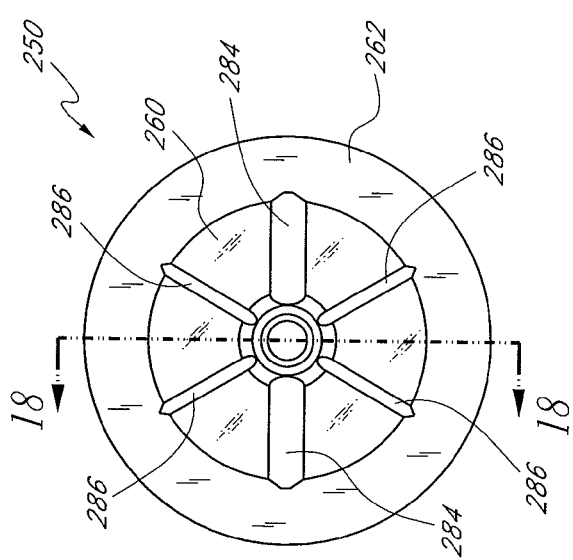
FIG. 19 is a front elevational view of the tracheostomy valve of FIG. 18.

FIGS. 18-20 illustrate another embodiment of the present tracheostomy valves. As with the embodiments described above, the valve 250 of FIGS. 18-20 includes a valve body 252, a rib 254 with a post 256 and biasing protrusions 258, a diaphragm 260 and a cap 262. However, the configurations of some of these components are substantially different from the embodiments described above. For example, the valve body 252 does not comprise an outer body and an inner body. Rather, the valve body 252 includes a substantially cylindrical proximal portion 264, and a distal portion 266 that flares outwardly and forms a bowl-shaped distal end of the valve body 252. A proximal end 268 of the valve body 252 is configured to receive an end of a tracheostomy tube (not shown) in an overlapping friction fit. An outer surface of the tube may engage an inner surface of the proximal end 268, or an inner surface of the tube may engage an outer surface of the proximal end 268. The proximal end 268 may include a taper, along the inside diameter or along the outside diameter or along both, to enhance the friction fit.

With reference to FIG. 18, the cap 262 comprises a wall that tapers slightly inwardly from a proximal end 270 to a distal end 272. At the distal end 272, the wall curls inwardly so that a cross-section of the wall resembles a J. The proximal end 270 of the cap 262 adjoins the distal portion 266 of the valve body 252. The distal portion 266 includes an annular ledge 274 extending around an outer surface thereof. The ledge 274 is formed by a step down in the wall thickness of the valve body 252. The cap 262 also includes a ledge 276 that is formed by a step down in its wall thickness. However, the ledge 276 on the cap 262 is formed around an inner surface thereof. Thus, the cap 262 mates with the distal portion 266 of the valve body 252 with the relatively thin-walled portions of each piece overlapping one another.

The cap 262 further includes a beveled outer edge 278 adjacent the proximal end 270. When the cap 262 and valve body 252 are assembled, the bevel 278 the ledge 274 on the valve body 252 together form a substantially V-shaped groove that extends around the outside circumference of the valve 250. The groove provides an advantageous location to apply a bead of adhesive to hold the cap 262 and valve body 252 together. However, those of ordinary skill in the art will appreciate that adhesive need not be used. The cap 262 and valve body 252 may be secured to one another through other techniques, such as a friction fit, ultrasonic welding, etc. Alternatively, adhesive may be applied in other areas, such as along the abutting faces of the relatively thin-walled portions of each piece.

The curled distal end 272 of the cap 262 forms a ring-shaped surface 280 that faces in the proximal direction and bears against the diaphragm 260. As in the previous embodiments, the diaphragm 260 is located between the cap 262 and the rib 254, with the post 256 extending through an aperture in the diaphragm 260 and the protrusions 258 bearing against the diaphragm 260. Portions of the diaphragm 260 may contact a distal edge 282 of the rib 254. The curled end surface 280 of the cap 262 and the protrusions 258 bias the diaphragm 260 into the concave/convex configuration described in detail above with respect to the previous embodiments.

With reference to FIG. 18, the curled distal end 272 of the cap 262 tapers inwardly in the distal-to-proximal direction, similar to the cap 40 of FIGS. 10-12. The taper advantageously facilitates laminar air flow, as discussed above with respect to the cap 40 of FIGS. 10-12. With reference to FIG. 19, in the illustrated embodiment the cap 262 includes six evenly spaced spokes 284, 286, with two of the spokes 284 being relatively thick and the remaining four spokes 286 being relatively thin. The spokes 284, 286 may include tapered side edges similar to those discussed above with respect to the cap 40 of FIGS. 10-12. The tapered side edges advantageously facilitate laminar air flow, as also discussed above. While in FIGS. 18-20 the wider spokes 284 are illustrated as being not aligned with the rib 254, those of ordinary skill in the art will appreciate the spokes 284, 286 may be aligned with the rib 254 in order to achieve the air flow advantages discussed above with respect to the valve 30 of FIG. 1.

SCOPE OF THE INVENTION

The above presents a description of the best mode contemplated for carrying out the present tracheostomy valves and related methods, and of the manner and process of making and using them, in such full, clear, concise, and exact terms as to enable any person skilled in the art to which they pertain to make and use these tracheostomy valves and related methods. These tracheostomy valves and related methods are, however, susceptible to modifications and alternate constructions from that discussed above that are fully equivalent. Consequently, these tracheostomy valves and related methods are not limited to the particular embodiments disclosed. On the contrary, these tracheostomy valves and related methods cover all modifications and alternate constructions coming within the spirit and scope of the tracheostomy valves and related methods as generally expressed by the following claims, which particularly point out and distinctly claim the subject matter of the tracheostomy valves and related methods.

What is claimed is:

1. A tracheostomy valve unit configured to cooperate with a tracheostomy tube insertable within a trachea of a patient, the valve unit comprising:

a valve body including a first end, a second end, a sidewall extending between the first end and the second end, and a fluid passageway extending from the first end to the second end, the first end operably connectable with a tracheostomy tube, the valve body comprising an inner body and an outer body connected to the inner body by a shoulder, the shoulder being spaced from the first end of the valve body;

a flexible diaphragm in the fluid passageway and spaced from the first end of the valve body, the diaphragm defining a plane;

a rib in the fluid passageway, the rib shaped substantially as a flat plate, at least a first portion of the rib abutting the diaphragm, at least a second portion of the rib abutting an inner surface of the outer body substantially orthogonal to the diaphragm, the rib defining a plane substantially perpendicular to the plane of the diaphragm; and a post integrally formed with the rib and extending distally from the rib, wherein the diaphragm comprises an aperture, and wherein the post extends through the aperture.

2. The valve unit of claim 1, wherein the plane of the rib intersects a center of the diaphragm.

3. The valve unit of claim 1, further comprising a cap cooperating with the second end of the valve body, wherein the cap includes an annular boss abutting the diaphragm.

4. The valve unit of claim 3, wherein the cap includes an outer rim, an inner hub, and a plurality of spokes extending between the hub and the rim.

5. The valve unit of claim 4, wherein at least a portion of the rim seats within the fluid passageway.

6. The valve unit of claim 3, wherein an inner surface of the fluid passageway includes an annular ledge, and wherein the rim abuts the ledge.

7. A valve unit comprising:
a proximal end;
a distal end;
an inner body having an inner surface inwardly obliquely angled towards the proximal end, the inner surface sloping from a first end of the inner body to a second end of the inner body, an interior portion of the inner body defining a fluid passageway;
an outer body inwardly obliquely angled towards the distal end;
a substantially planar rib extending at least partially across the inner body, a distal portion of the rib comprising biasing protrusions, a distal edge of the rib being proximate the distal end of the valve unit:
an inner ledge proximate to the distal end;
a cap proximate the distal end of the valve unit and having an outermost periphery inside the valve body and comprising a rim abutting the inner ledge, the cap comprising an annular boss;
a diaphragm in contact with and between the boss of the cap and the biasing protrusions of the rib, the rib substantially transverse to the diaphragm; and
a post integrally formed with the rib and extending distally from the rib, wherein the diaphragm comprises an aperture, and wherein the post extends through the aperture.

8. The valve unit of claim 7, further comprising a plurality of splines between the inner body and the outer body.

9. The valve unit of claim 7, further comprising a flange extending radially outward from a distal end of the outer body.

10. The valve unit of claim 7, wherein the rib is integral with the inner body.

11. The valve unit of claim 7, wherein the rib extends fully across the inner body.

12. The valve unit of claim 7, wherein the cap comprises a plurality of spokes, at least some said spokes being thicker than other said spokes, wherein the thicker spokes are aligned with the rib.

13. The valve unit of claim 12, wherein the cap includes a key configured to align the thicker spokes and the rib.

14. The valve unit of claim 7, wherein the cap comprises surfaces configured to facilitate laminar flow through the valve unit.

15. The valve unit of claim 7, wherein the cap comprises a hub comprising a recess, and wherein the post extends into the recess.

* * * * *